US007405238B2

(12) United States Patent
Markey et al.

(10) Patent No.: US 7,405,238 B2
(45) Date of Patent: Jul. 29, 2008

(54) PHARMACOLOGICAL INDUCEMENT OF THE FED MODE FOR ENHANCED DRUG ADMINISTRATION TO THE STOMACH

(75) Inventors: Micheline Markey, Santa Cruz, CA (US); John W. Shell, Hillsborough, CA (US); Bret Berner, El Granada, CA (US)

(73) Assignee: Depomed Inc., Menlo Park, CA (US)

( * ) Notice: Subject to any disclaimer, the term of this patent is extended or adjusted under 35 U.S.C. 154(b) by 95 days.

(21) Appl. No.: 10/235,076

(22) Filed: Sep. 4, 2002

(65) Prior Publication Data
US 2003/0044466 A1 Mar. 6, 2003

Related U.S. Application Data

(62) Division of application No. 09/432,881, filed on Nov. 2, 1999.

(51) Int. Cl.
*A61K 31/21* (2006.01)
*A61K 47/00* (2006.01)

(52) U.S. Cl. ...................................... 514/513; 424/439
(58) Field of Classification Search ................ 514/892, 514/513, 584; 424/439
See application file for complete search history.

(56) References Cited

U.S. PATENT DOCUMENTS

| | | | |
|---|---|---|---|
| 3,492,131 A | 1/1970 | Schlatter et al. | |
| 3,689,486 A | 9/1972 | Clauss et al. | |
| 3,714,159 A | 1/1973 | Janssen et al. | |
| 3,914,434 A * | 10/1975 | Bohni | 514/738 |
| 3,916,899 A | 11/1975 | Theeuwes et al. | |
| 4,470,980 A | 9/1984 | Higuchi et al. | |
| 4,871,546 A | 10/1989 | Feltz et al. | |
| 5,043,328 A | 8/1991 | Weithmann | |
| 5,213,794 A | 5/1993 | Fritsch et al. | |
| 5,328,697 A | 7/1994 | Raman et al. | |
| 5,340,590 A | 8/1994 | Wong et al. | |
| 5,427,798 A | 6/1995 | Ludwig et al. | |
| 5,516,524 A * | 5/1996 | Kais et al. | 424/439 |
| 5,686,094 A | 11/1997 | Acharya | |
| 5,938,654 A | 8/1999 | Wong et al. | |

FOREIGN PATENT DOCUMENTS

| | | | |
|---|---|---|---|
| DE | 3217071 A1 | 11/1983 | |
| EP | 0571217 A2 | 11/1993 | |
| EP | 0715846 A1 | 6/1996 | |
| EP | 1029892 A1 | 8/2000 | |
| GB | 1330829 | 9/1973 | |
| WO | WO 97/47285 A1 | 12/1997 | |
| WO | WO 99/25321 A1 | 5/1999 | |

OTHER PUBLICATIONS

MacKenzie et al, 113:CA96305, 1990.*
Sund et al., Glucose and Cation Transport in Rat Jejunum. Ileum and Colon in vivo; Acta. Pharmacol. et Toxicol. 1978, 42:253-258.
Fox et al., Surfactants Selectively Ablate Enteric Neurons of the Rat Jejunum, J. Pharmacol. & Exptl. Therapeutics 1983, 227: 538-544.
MacKenzie et al., Three-Generation Reproduction Study with Dioctyl Sodium Sulfosuccinate in Rats; Fundamental and Applied Toxicology 1990, 15:53-62.
Efentakis et al., "The influence of surfactants on drug release from a hydrophobic matrix," International Journal of Pharmaceutics, 1991, pp. 153-158, vol. 70(1-2).
Stephens et al., "Osmolyte and tryptophan receptors controlling gastric emptying in the dog," American Journal of Physiology, 1976, pp. 848-853, vol. 231.
Groning et al., Drug Development and Industrial Pharmacy, 10:4:527-539 (1984).
Groning et al., International Journal of Pharmaceutics 56:11-16 (1989).
Binder, Colonic Secretion; chapter 39 of Physiology of the Gastrointestinal Tract, vol. 2 (Johnson et al., ed.) (Raven Press, New York 1981), pp. 1003-1019.
Moes, Gastroretentive Dosage Forms, Critical Reviews in Therapeutic Drug Carrier Systems, 1993, vol. 10 pp. 143-195.

* cited by examiner

*Primary Examiner*—San-ming Hui

(57) ABSTRACT

Drugs intended for absorption in the stomach or upper intestinal tract are administered in oral drug delivery systems in conjunction with any of various substances that have been discovered to function as potent agents for inducing the fed mode. By inducing the onset of the fed mode, these agents cause the stomach to prolong its retention of the drug delivery system, which is either large enough to be retained in the stomach during the fed mode or swells or expands to such a size upon ingestion. The fed mode inducing agents include the following compounds and their salts: glycine and glycylglycine, xylitol and related sugar alcohols, sodium and other metal docusates, β-casomorphins, α-lipoic acid and similarly structured acids, 2,2-diaryl-4-(4'-aryl-4'-hydroxypipendino) butyramides, arginine, Trp-Trp, alkylpyridinium halides, dihydroxybenzoic acids, and potent sweeteners such as aspartame, aspartic acid, acesulfame, and stevioside.

5 Claims, No Drawings

PHARMACOLOGICAL INDUCEMENT OF THE FED MODE FOR ENHANCED DRUG ADMINISTRATION TO THE STOMACH

CROSS-REFERENCE TO RELATED APPLICATIONS

This is a divisional of Application Ser. No. 09/432,881 filed Nov. 2, 1999.

BACKGROUND OF THE INVENTION

1. Field of the Invention

This invention is in the general field of pharmacology, and relates in particular to oral dosage formulations that deliver drugs by controlled release in the stomach for a prolonged period of time.

2. Description of the Prior Art

Many drugs have their greatest therapeutic effect when released in the stomach, particularly when the release is prolonged in a continuous, controlled manner. Drugs delivered in this manner cause less side effects and provide their therapeutic effects without the need for repeated dosages, or with a low dosage frequency. Localization of the drug delivery in the stomach is an advantage for the treatment of local disorders of the stomach such as esophageal reflux disease, for the eradication of ulcer-causing bacteria in the gastric mucosa, and for the treatment of disorders that require sustained antacid action. Sustained release in the stomach is also useful for therapeutic agents that the stomach does not readily absorb, since sustained release prolongs the contact time of the agent in the stomach or in the upper part of the small intestine, which is where absorption occurs and contact time is limited. Under normal or average conditions, for example, material passes through the small intestine in as little as 1 to 3 hours. For drugs that are absorbed almost exclusively in the small intestine, such as captopril and the cephalosporins, this short contact time limits the bioavailability of these drugs, particularly when the drugs are administered in a controlled-release dosage form.

The passage of matter through the stomach can be delayed in the normal digestive process by the physiological condition that is variously referred to as the digestive mode, the postprandial mode, or the "fed mode" (the latter term is used in the remainder of this specification for convenience). When the stomach is not in this mode, it is in the interdigestive or "fasting" mode. The difference between the two modes lies in the pattern of gastroduodenal motor activity.

In the fasting mode, the stomach exhibits a cyclic activity called the interdigestive migrating motor complex (IMMC). This activity occurs in four phases:

In Phase I, which lasts 45 to 60 minutes and is the most quiescent, few or no contractions occur.

In Phase II, irregular intermittent sweeping contractions occur that gradually increase in magnitude.

In Phase III, intense bursts of peristaltic waves appear in both the stomach and the small bowel. This lasts for 5 to 15 minutes.

Phase IV is a transition period of decreasing activity which lasts until the next cycle begins.

The total cycle time is approximately 90 minutes, and the contents of the stomach are swept out by the powerful peristaltic waves that occur during Phase III. Phase III of the IMMC thus functions as an intestinal housekeeper, sweeping swallowed saliva, gastric secretions, food particles, and particulate debris to the small intestine and colon, and preparing the upper tract for the next meal while preventing bacterial overgrowth. Pancreatic exocrine secretion of pancreatic peptide and motilin also cycle in synchrony with the motor pattern.

The fed mode is induced by nutritive elements immediately after food ingestion, and begins with a rapid and profound change in the motor pattern of the upper gastrointestinal GI tract, the change occurring over a period of 30 seconds to one minute. The change occurs almost simultaneously at all sites of the GI tract, before the stomach contents have reached the distal small intestine. Once the fed mode is established, the stomach generates 3-4 continuous and regular contractions per minute, similar to those of the fasting mode but of about half the amplitude. The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 6 hours.

The minimum particle size that will be retained in the stomach is thus substantially smaller in the fed mode than in the fasting mode. Particles large enough to be retained in the fasting mode are too large for practical administration in most patients. Particles of a smaller particle size can be retained in the stomach if they are administered to a patient who is in the fed mode, and this serves as an effective and feasible means of prolonging the residence time of these particles in the stomach.

While onset of the fed mode is normally caused by the ingestion of a meal, the use of a meal as a means of prolonging the residence time of a drug in the stomach has certain disadvantages. One disadvantage is a lack of reliability, since although a variety of nutritive elements are capable of inducing the fed mode, different individuals consume meals of different compositions, some inducing the fed mode more easily and for different durations than others. Another disadvantage is that many drugs are adversely affected by the presence of food in the stomach. Thus, a meal-induced fed mode can increase the absorption of some drugs, while decreasing the absorption of others. These disadvantages are avoided by inducing the fed mode through means other than the ingestion of a meal.

While the fed mode promotes the retention of relatively small particles in the stomach, there are still many patients for whom even these particles are too large to be comfortably ingested. For these patients, particles that are initially small enough for comfortable ingestion and swell to a larger size upon contact with the gastric fluid in the stomach can be used. The swelling can occur as a result of hydration of the particle material upon absorption of water from the gastric fluid. Alternatively, the swelling can occur as a result of gas generation, such as carbon dioxide for example, by contact of gastric fluid with the dosage form, the gas generation occurring in a membrane bag or otherwise within the dosage form. A still further alternative is the use of a large tablet held in a compressed condition by mechanical tension within a small capsule and released to expand to its full relaxed size when the capsule contacts gastric fluid. Whether the particles are large enough for fed mode retention before they are ingested or reach that size by swelling or expansion in the stomach, it is important that the particles retain their size while the drug is released into the gastric fluid. Thus, release of the drug must not itself cause the particle to shrink below the minimum size required for retention in the fed mode. Also, the quantity of drug in the formulation should be controllable independently of the particle size. Thus, while the particles must be large enough to be retained in the stomach and contain enough inert carrier to maintain their size during drug release, there should be no need for the patient to ingest a large number of particles to achieve the needed drug dose.

The need for administering and maintaining particles of appropriate size has been addressed by U.S. Pat. No. 5,007,790 ("Sustained Release Oral Drug Dosage form," Shell, inventor, Apr. 16, 1991). This patent discloses particle-form oral drug delivery systems in which the particles are small when taken orally but swell in the gastric fluid to a diameter of approximately 8 to 11 mm. Swelling to this size requires approximately two hours. Retention of the particles in the stomach while they are swelling requires that the patient be in the fed mode when the drug is administered, or at least that the swelling occur before the Phase III IMMC waves of the fasting mode begin. With control of the IMMC waves dependent on the timing of the fed mode and the manner in which the fed mode is induced, the particle size and retention are subject to uncertainty, and the duration of the retention is at times, and in some individuals, less than desired.

Induction of the fed mode by pharmacological means is reported in the literature, particularly by J. N. Hunt and his co-workers (*J. Physiol.* 201:327(1968)). The most potent pharmacological agents reported for this purpose are straight-chain fatty acids with optimal activity at a chain length in the vicinity of 12 carbons. Use of these agents for maintaining the fed mode for a period of hours in dogs or humans, however, requires dosages in the range of 0.5 g to 1 g. Other agents that have been reported to induce the fed mode are glucose and tryptophan, but these require even higher dosages. John Stephens and co-workers (*Am. J Physiol.* (1976) 231:848-853 and *Gastroenterol.* (1975) 69:920-927) reported that amino acids such as glycine, arginine and tryptophan slowed gastric emptying in dogs when administered in excess of 1 g similar to results obtained for glucose. The literature reports that all of these agents, with the exception of tryptophan, slow gastric emptying by their osmolarity and consequently fail to suggest any potent specific agents. The low potency of these reported agents makes it difficult to incorporate them in effective amounts in a sustained-release oral dosage form such as a capsule or tablet since the capsule or tablet must be small enough for ingestion and yet contain effective amounts of the agent, the drug, and any excipients needed for controlling the release of the drug.

R. Groning and G. Heun (*Drug Dev. Ind. Pharm.* 10:527 (1984) and *Int. J. Pharmaceut.* 56:111 (1989)) incorporated salts of myristic acid (the 14-carbon fatty acid) into a double capsule or two-layer immediate release dosage form containing either riboflavin or nitrofurantoin as active drugs. These salts are not of high potency, however, and the amounts administered, 107.5-165 mg per dosage form, had only a marginal effect on gastric retention, increasing the retention time by only about 1 to 2 hours. An agent that can be incorporated into a dosage form at a low dose and yet achieve a mean gastric retention time of 4-6 hours similar to food has not been reported.

SUMMARY OF THE INVENTION

The present invention resides in the discovery of the ability of certain potent substances to cause pharmacological inducement of the fed mode in a patient. These substances, hereinafter referred to as "fed-mode inducing agents," thus serve as a novel means of inducing the fed mode that does not rely on the ingestion of a meal. These agents can be administered separately or combined with a drug in a single dosage form. When combined with a drug, the agents are sufficiently potent that they can be incorporated into sustained-release drug delivery systems of a size practical to swallow. Included among such delivery systems are unit oral dosage forms that contain both the fed-mode inducing agent and the drug supported by a solid matrix that is sufficiently large to promote retention in the stomach during the fed mode or that swells to such a size upon imbibition of water. The fed-mode inducing agents of this invention are as follows.

(a) glycine, glycylglycine, and salts of either of these two compounds
(b) $C_4$-$C_8$ sugar alcohols
(c) alkali and alkaline earth metal docusates
(d) β-casomorphins
(e) dithioorganic acids of the formula

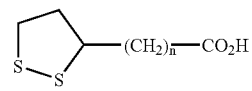

in which n is 3 to 13

(f) 2,2-diaryl-4-(4'-aryl-4'-hydroxypiperidino)butyramides of the formula

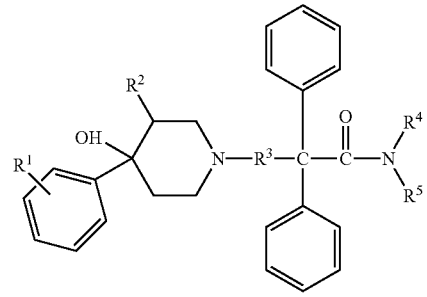

in which:
 $R^1$ is H, lower alkyl, or halo,
 $R^2$ is H or methyl,
 $R^3$ is —$CH_2CH_2$— or —$CH(CH_3)CH_2$—,
 $R^4$ is lower alkyl, and
 $R^5$ is lower alkyl (g) arginine and its salts
(h) the dipeptide tryptophan-tryptophan ("Trp-Trp") and its salts
(i) alkyl pyridinium halides of the formula

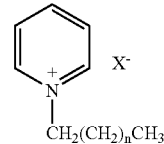

in which n is 8 to 20 and X is halide
(j) dihydroxybenzoic acids and highly potent food sweeteners, such as
 (k) stevioside
 (l) aspartame and other alkyl esters of N—L—α-aspartyl L-phenylalanine (m) aspartic acid and its salts (n) 3,4-dihydro-1,2,3-oxathiazin-4-ones of the formula

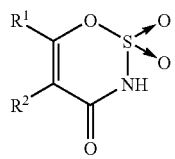

in which $R^1$ and $R^2$ are the same or different and each is either a hydrogen atom or an alkyl group having no more than ten carbon atoms, and salts of these 3,4-dihydro-1,2,3-oxathiazin-4-ones In certain embodiments of this invention, the fed mode inducing agent is incorporated into a sustained-release drug delivery system that combines the benefits of swellable particles with a pharmacologically induced fed mode to retain the drug delivery system in the stomach of the patient independently of the dietary habits or digestive cycles of the patient. Drug administration is thereby achieved with a high level of control over the site of drug delivery. The invention in these embodiments is a single dosage form for oral administration that includes both a solid-state drug dispersed or otherwise retained in a solid matrix of a water-swellable polymer, and one or more of the fed mode inducing agents listed above. The water-swellable polymer matrix is in the form of particles that are small enough for oral administration yet rapidly swell upon imbibition of water from gastric fluid to a size sufficiently large that they are retained in the stomach for several hours during the fed mode. The swollen particles maintain their size long enough to be held in the stomach for the desired duration of drug delivery, which is generally in excess of several hours. The matrix may be susceptible to decomposition by the action of components in the gastric fluid, or it may tend to dissolve in the gastric fluid, but in either case at a rate slow enough to maintain the retention-promoting size for the desired duration. The drug itself is usually soluble or partially soluble in gastric fluid, yet is released from the matrix into the fluid at a limited rate due to the characteristics of the matrix. The fed mode releasing agent may be incorporated into the dosage form, or applied as a separate layer or coating over the dosage form, in a manner that will cause the agent to be released immediately upon contact with the gastric fluid, thereby imparting its full effect of inducing the fed mode as soon as the dosage form reaches the stomach. Alternatively, the agent may be formulated or incorporated in a manner that will result in prolonged or sustained release of the agent itself, thereby imparting its fed mode inducing effect in a continuous and sustained manner.

In other embodiments of this invention, the fed mode inducing agent is administered in a non-swelling matrix either prior to or concurrently with the drug of interest, the fed mode inducing agent and the drug being in separate dosage forms. Administered in this manner, the agent can still improve the bioavailability of drugs formulated for immediate release and of many drugs that are administered as powders. When administered in a dosage form separate from the drug, the agent can be incorporated in a tablet or capsule, which can be immediate release or sustained release. When the drug and said agent are incorporated in the same dosage form, the drug and agent can occupy different layers or regions of a capsule or tablet or the two may be blended together in the dosage form. The dosage form which is sufficiently large to be retained in the stomach in the fed mode may be a large non-swelling tablet, a swelling tablet, an osmotic pump, a hydrogel or other type of dosage form that swells or expands upon contact with gastric fluid, or another sustained-release dosage form.

This invention further resides in pharmaceutical compositions containing a drug retained in a solid matrix whose size is sufficiently large to promote the retention of the matrix in the stomach during the fed mode, in combination with a pharmacological fed mode inducing agent that is retained in a solid matrix, enclosure, or other material or device that is configured to release the fed mode inducing agent into the stomach in a sustained manner. Fed mode inducing agents contemplated for this aspect of the invention are those whose potency is sufficiently great that onset of the fed mode occurs upon release of as little as 500 mg of the agent or less.

Details of these and other features and embodiments of the invention are provided below.

DETAILED DESCRIPTION OF THE INVENTION AND SPECIFIC EMBODIMENTS

One group of fed mode inducing agents of this invention is glycine, glycylglycine and salts thereof. The formulas of prominent members of this group are as follows

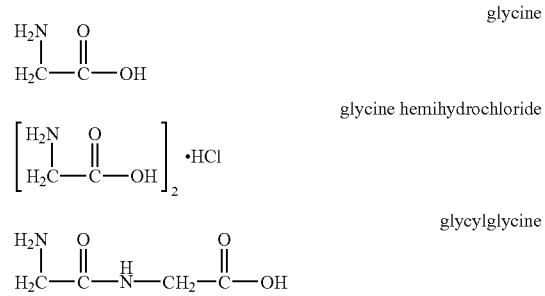

Preferred amounts of this agent in an oral drug unit dosage form are in the range of about 1 mg to about 500 mg. In the most preferred embodiments of this invention when this agent is used, the amount ranges from about 5 mg to about 150 mg.

Further fed mode inducing agents of this invention are those of the group defined as sugar alcohols, which are polyols of the general formula

in which n is a positive integer. Of particular interest are $C_4$-$C_8$ sugar alcohols, i.e., those of this formula in which n is 2 to 6. Xylitol, whose formula is

is a preferred member of this group. Preferred amounts of sugar alcohols in an oral drug unit dosage form are in the range of about 30 mg to about 1000 mg. In the most preferred embodiments of this invention when this agent is used, the amount ranges from about 100 mg to about 800 mg.

The alkali and alkaline earth metal docusates of this invention are structures in which the anion has the formula

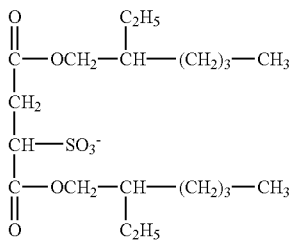

and the cation is either an alkali metal ion or an alkaline earth metal ion. Calcium and sodium docusates are preferred, and sodium docusate is particularly preferred. Preferred amounts of alkali and alkaline earth metal docusates in an oral drug unit dosage form are in the range of about 30 mg to about 1000 mg. In the most preferred embodiments of this invention when this agent is used, the amount ranges from about 50 mg to about 400 mg.

The β-casomorphins of this invention include the naturally occurring peptides released from β-casein by the action of acid and pepsin. These naturally occurring peptides include both bovine and human β-casomorphins. The sequence of bovine β-casomorphin is Tyr-Pro-Phe-Pro-Gly-Pro-Ile, while the sequence of human β-casomorphin is Tyr-Pro-Phe-Val-Glu-Pro-Ile. Also included are fragments and synthetic derivatives and analogs of β-casomorphins that have μ-opioid activity and improved stability in the GI tract to acid and peptidases. These include, but are not limited to, Tyr-Pro-Phe, Tyr-Pro-Phe-amide, Tyr-D-Ala-Phe-amide, Tyr-D-Ala-Phe-D-Pro-Tyr-amide, Tyr-D-Ala-Phe-Pro-Tyr-amide, Tyr-D-Ala-Phe-D-Ala-Tyr-amide, Tyr-Pro-Phe-Pro, Tyr-Pro-Phe-Pro-amide, Tyr-D-Ala-Phe-(pCl)Phe-Pro-amide, Tyr-D-Ala-Phe-Pro-amide, Tyr-Pro-Val-Pro-amide, Tyr-Pro-Phe-Pro-Gly-amide, Tyr-D-Ala-Phe-Pro-Gly-amide, Tyr-D-Pro-Phe-Pro-Gly-amide, Tyr-Pro-Phe-Pro-Gly, Tyr-Pro-Phe-Pro-Gly-Pro, Tyr-Pro-Phe-Pro-amide, Pro-Phe-Pro-Gly-Pro-Ile, Tyr-Pro-(nMe)Phe-D-Pro-amide, and Tyr-Pro-Phe-D-Pro-amide. Preferred amounts of β-casomorphins in an oral drug unit dosage form are in the range of about 1 mg to about 300 mg. In the most preferred embodiments of this invention when an agent of this class is used, the amount ranges from about 5 mg to about 150 mg.

Of the dithioorganic acids of this invention, whose generic formula is shown above, the preferred example is α-lipoic acid, the formula of which is

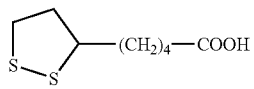

Preferred amounts of dithioorganic acids in an oral drug unit dosage form are in the range of about 30 mg to about 1000 mg. In the most preferred embodiments of this invention when this agent is used, the amount ranges from about 40 mg to about 300 mg.

The 2,2-diaryl-4-(4'-aryl-4'-hydroxypiperidino)butyramides of this invention, whose generic formula is given above, are synthetic opiates. In the definitions associated with this formula, the term "lower alkyl" denotes $C_1$-$C_6$ alkyl, preferably $C_1$-$C_3$ alkyl, more preferably methyl or ethyl, and "halo" denotes fluoro, chloro, bromo, or iodo, preferably fluoro or chloro, and most preferably chloro. Preferred species are those in which $R^1$ is halo, more preferably 4-halo, still more preferably 4-fluoro or 4-chloro, and $R^4$ and $R^5$ are each either methyl or ethyl. A specific example of a species within the generic formula is 4-(p-chlorophenyl)-4-hydroxy-N,N-dimethyl-α,α-diphenyl-1-piperidinebutyramide, which bears the generic name loperamide and is generally available as a monohydrochloride salt. Loperamide is commercially available from Ortho Pharmaceutical Corporation, Raritan, N.J., USA, under the name IMODIUM as a therapeutic agent for controlling diarrhea. The formula for loperamide is

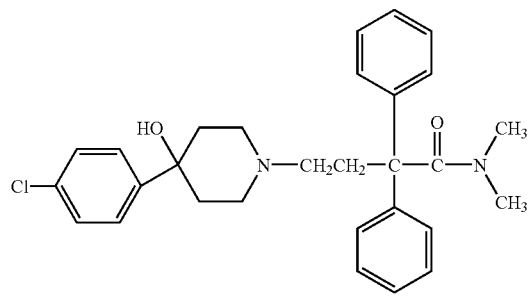

This compound and other 2,2-diaryl-4-(4'-aryl-4'-hydroxypiperidino)butyramides are disclosed in U.S. Pat. No. 3,714,159 (Janssen et al., Jan. 30, 1973), the contents of which are incorporated herein by reference. Preferred amounts of the 2,2-diaryl-4-(4'-aryl-4'-hydroxypiperidino)butyramides for use in an oral drug unit dosage form in accordance with the present invention are in the range of about 0.5 mg to about 300 mg. In the most preferred embodiments of this invention when this agent is used, the amount ranges from about 2 mg to about 15 mg.

Arginine has the formula

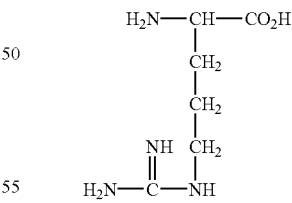

Preferred amounts of arginine in an oral drug unit dosage form are in the range of about 3 mg to about 300 mg. In the most preferred embodiments of this invention when this agent is used, the amount ranges from about 30 mg to about 250 mg.

Salts of glycine and arginine that are suitable for this invention include nontoxic salts, preferably cationic salts and hydrohalide or hemihydrohalide salts. The sodium, potassium, calcium, hemihydrochloride, and hydrochloride salts are the most preferred examples.

The peptide Trp-Trp has the formula

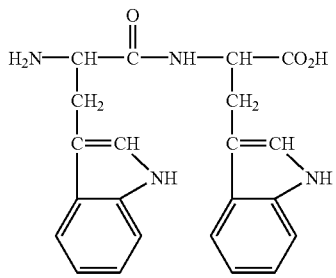

Preferred amounts of Trp-Trp in an oral drug unit dosage form are in the range of about 0.05 mg to about 300 mg. In the most preferred embodiments of this invention when this agent is used, the amount ranges from about 0.5 mg to about 10 mg.

Salts of Trp-Trp that are suitable for this invention include nontoxic salts, preferably cationic salts and hydrohalide or hemihydrohalide salts. The sodium, potassium, calcium, hemihydrochloride, and hydrochloride salts are the most preferred examples.

Of the alkyl pyridinium halides of this invention, whose formula is shown above, the preferred examples are those in which n is 12 to 16 and, separately, those in which X is chloride, or those in which both n is 12 to 16 and X is chloride. A particularly preferred alkyl pyridinium halide is cetyl pyridinium chloride in which n is 14 and X is Cl. Preferred amounts of alkyl pyridinium halides in an oral drug unit dosage form are in the range of about 0.1 mg to about 200 mg. In the most preferred embodiments of this invention when this agent is used, the amount ranges from about 0.5 mg to about 50 mg.

Of the dihydroxybenzoic acids of this invention, the preferred example is gentisic acid or its natural source gentian root. The chemical name of gentisic acid is 2,5-dihydroxybenzoic acid, of the formula

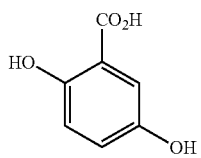

Preferred amounts of dihydroxybenzoic acids in an oral drug unit dosage form are in the range of about 3 mg to about 300 mg. In the most preferred embodiments of this invention when this agent is used, the amount ranges from about 10 mg to about 100 mg.

The sweetener stevioside has the generic name 13-[(2-O-β-D-glucopyranosyl-α-D-glucopyranosyl)oxy]kaur-16-en-18-oic acid β-glucopyranosyl ester, and the formula

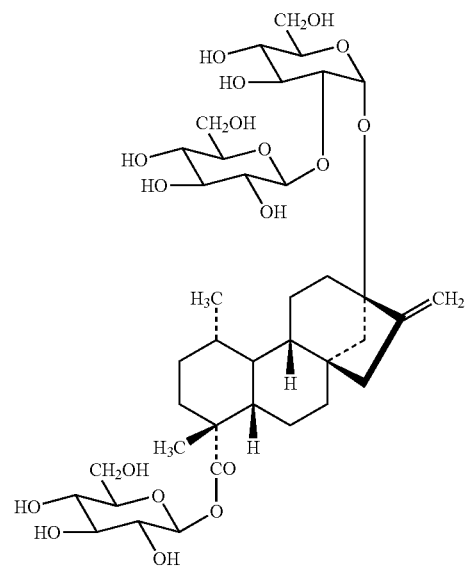

The alkyl esters of N-L-α-aspartyl L-phenylalanine have the generic formula:

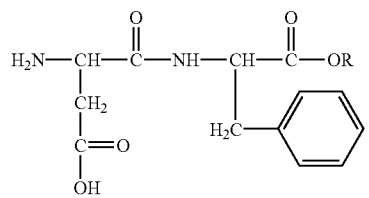

in which R is lower alkyl, preferably $C_1$-$C_4$ alkyl. Aspartame is the methyl ester, i.e., the species in which R is a methyl group.

Aspartic acid has the formula

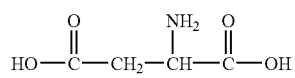

Of the 3,4-dihydro-1,2,3-oxathiazin-4-ones of the invention, whose formula is shown above, a preferred group is those in which $R^1$ and $R^2$ (independently) are either H or $C_1$-$C_4$ alkyl, and a more preferred group is those in which $R^1$ is $C_1$-$C_4$ alkyl and $R^2$ is H. The most preferred example is that in which $R^1$ is methyl and $R^2$ is H. This compound is known as acesulfame and by the generic name 6-methyl-1,2,3-oxathiazin-4(3H)-one 2,2-dioxide. Suitable salts of 3,4-dihydro-1,2,3-oxathiazin-4-ones for use in this invention are nontoxic salts, particularly cationic edible salts. The potassium, sodium, and calcium salts are preferred, particularly as salts of acesulfame.

Of the sweeteners of this invention, the most preferred is aspartame. Preferred amounts of these sweeteners in an oral drug dosage form are in the range of about 30 mg to about 800 mg. In the most preferred embodiments of this invention where sweeteners are used, the amount ranges from about 50 mg to about 400 mg.

Fed mode inducing agents in accordance with this invention can be incorporated in the dosage forms in any of various ways. An agent may, for example, be incorporated in such a manner that the agent is released substantially immediately into the gastric fluid as soon as the dosage form enters the stomach. Alternatively, an agent may be incorporated in such a manner that it is released into the gastric fluid in a sustained manner, such as by dissolution and diffusion out of a solid matrix in which the agent is retained, or by slow erosion of the solid matrix. A still further alternative is a combination whereby a portion of the agent is released immediately and the remainder is released in a sustained manner. In either case, the drug itself is preferably retained in a solid matrix that releases the drug from the matrix in a sustained (i.e., continuous and prolonged) manner.

Solid matrices that provide sustained release of substances (drugs, fed mode inducing agents, or both) in the practice of this invention may assume any of various forms. One form is a solid mass impregnated with the substance(s) and releasing the substance(s) either by dissolution of the substance(s) into gastric fluid that is gradually imbibed by the matrix mass and diffusion of the dissolved substance(s) out of the mass. Another is a solid mass impregnated with the substance(s), the mass itself being gradually erodible upon contact with gastric fluid and releasing the substance(s) by the process of erosion. A third is an osmotic dispensing device, which is a compartmented enclosure with one compartment containing the substance(s) to be dispensed and another (or part of the same compartment) that has a permeable wall through which gastric fluid enters by osmosis. When the device contains separate compartments, they are separated by a flexible or movable wall, and the entering gastric fluid forces the substance out of the enclosure through a dispensing port. Dispensing of the substance(s) thus occurs by osmotic pressure. Disclosures of osmotic dispensing devices of this general type are found in U.S. Pat. No. 3,916,899 (inventors Theeuwes, Felix, et al., issue date Nov. 4, 1975), U.S. Pat. No. 5,340,590 (inventors Wong, Patrick S. L., et al., issue date Aug. 23, 1994), and U.S. Pat. No. 5,938,654 (inventors Wong, Patrick S. L., et al., issue date Aug. 17, 1999). The disclosures of each of these patents are incorporated herein by reference.

For fed mode inducing agents that are released substantially immediately into the gastric fluid, either in whole or in part, such immediate release can be achieved by placing most, and preferably all, of the fed mode enhancing agent outside the matrix that retains the drug. One way of achieving this is by including the agent in a solid layer or solid coating over the matrix. Another way is by adding the agent in powdered form to a capsule that also contains the particles of the drug-containing matrix.

When the fed mode inducing agent is contained in a solid layer or coating, the layer or coating preferably consists of the agent retained in a water-soluble matrix that rapidly disintegrates upon contact with the gastric fluid and thereby releases the agent into the fluid. Typical classes of film-forming matrices are cellulosics, vinyls, glycols, acrylics, and other carbohydrates. Examples of cellulosics are hydroxpropyl-methycellulose, hydroxypropylcellulose, hydroxyethylcellulose, carboxymethylcellulose, ethyl cellulose, and microcrystalline cellulose. Examples of vinyls are polyvinylpyrrolidone, crospovidone, and polyvinyl alcohol. Examples of glycols are polyethylene glycols, polyethylene oxides, sodium starch glycolate, and poloxamers. Examples of acrylates are dimethylaminoethylmethacrylate, methacrylic acid copolymers and ethyl acrylate-methyl methacrylate copolymers. Examples of other carbohydrates are maltodextrins, polydextrose, lactose and zein. Sodium starch glycolate and microcrystalline cellulose are particularly preferred. The proportion of the fed mode inducing agent in the water-soluble matrix can vary widely and is not critical. In most cases, however, best results will be obtained with a weight ratio of agent to total water-swellable matrix in the dosage form ranging from about 0.5:8 to about 3:5, and preferably from about 1:8 to about 2:8. For highly potent agents, ratios that are considerably lower can be used.

While the preferred amounts of each type of fed mode inducing agent in accordance with this invention are stated above, the amount of the fed mode inducing agent used in general in conjunction with an oral drug dosage form is not critical to this invention. Optimal amounts will vary with the type of agent used. For embodiments of the invention in which the drug matrix is a water-swellable polymer, the appropriate amount of fed mode inducing agent for any particular dosage form will be the amount that will induce and maintain the fed mode long enough for the particles of water-swellable polymer to reach a size that is large enough to be retained in the stomach in the fed mode.

When sustained (i.e., continuous and prolonged) release of the fed mode inducing agent is desired, the agent can be retained in a solid matrix such as the described above for the drug, and therefore released from the matrix by dissolution and diffusion, or by slow erosion of the matrix itself. The agent and the drug may thus both be retained in a common solid matrix, or they may be retained in separate solid matrices, each forming a distinct layer of a single tablet, or separate tablets. Placement of the agent and drug in separate matrices permits the use of different matrices to achieve different release rates or profiles of the drug and the agent.

In those embodiments of the invention in which the matrix (containing either the drug, the fed mode inducing agent, or both) is a water-swellable polymer, the polymer is any polymer that is non-toxic, that swells in a dimensionally unrestricted manner upon imbibition of water, and that provides for sustained release of an incorporated ingredient. Examples of polymers suitable for use in this invention are cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), polysaccharide gums, maleic anhydride copolymers, poly(vinyl pyrrolidone), starch and starch-based polymers, poly (2-ethyl-2-oxazoline), poly(ethyleneimine), polyurethane hydrogels, and crosslinked polyacrylic acids and their derivatives. Further examples are copolymers of the polymers listed in the preceding sentence, including block copolymers and grafted polymers. Specific examples of copolymers are PLURONIC® and TECTONIC®, which are polyethylene oxide-polypropylene oxide block copolymers available from BASF Corporation, Chemicals Div., Wyandotte, Mich., USA.

The terms "cellulose polymer" and "cellulosic polymer" are used herein to denote linear polymers of anhydroglucose. Preferred cellulosic polymers are alkyl-substituted cellulosic polymers that ultimately dissolve in the gastrointestinal (GI) tract in a predictably delayed manner. Preferred alkyl-substituted cellulose derivatives are those substituted with alkyl groups of 1 to 3 carbon atoms each. Examples are methylcellulose, hydroxymethylcellulose, hydroxyethylcellulose, hydroxypropylcellulose, hydroxypropylmethylcellulose, and carboxymethylcellulose. In terms of their viscosities, one class of preferred alkyl-substituted celluloses includes those whose viscosity is within the range of about 100 to about 110,000 centipoise as a 2% aqueous solution at 20° C. Another class includes those whose viscosity is within the range of about 1,000 to about 4,000 centipoise as a 1% aqueous solution at 20° C. Particularly preferred alkyl-substituted celluloses are hydroxyethylcellulose and hydroxypropylmethylcellulose. A presently preferred hydroxyethylcellulose is NATRASOL® 250HX NF (National Formulary), available from Aqualon Company, Wilmington, Del., USA.

Polyalkylene oxides of greatest utility in this invention are those having the properties described above for alkyl-substituted cellulose polymers. A particularly preferred polyalkylene oxide is poly(ethylene oxide), which term is used herein to denote a linear polymer of unsubstituted ethylene oxide. For agents having high solubility in water, poly(ethylene oxide) polymers having molecular weights of about 4,000,000 and higher are preferred. More preferred are those with molecular weights within the range of about 4,500,000 to about 10,000,000, and even more preferred are polymers with molecular weights within the range of about 5,000,000 to about 8,000,000. Preferred poly(ethylene oxide)s are those with a weight-average molecular weight within the range of about $1 \times 10^5$ to about $1 \times 10^7$, and preferably within the range of about $9 \times 10^5$ to about $8 \times 10^6$. Poly(ethylene oxide)s are often characterized by their viscosity in solution. For purposes of this invention, a preferred viscosity range is about 50 to about 2,000,000 centipoise for a 2% aqueous solution at 20° C. Two presently preferred poly(ethylene oxide)s are POLYOX® NF, grade WSR Coagulant, molecular weight 5 million, and grade WSR 303, molecular weight 7 million, both products of Union Carbide Chemicals and Plastics Company Inc. of Danbury, Conn., USA. Two other preferred poly(ethylene oxide)s are POLYOX® NF, grade WSR 301, molecular weight 4 million, and grade WSR N60K, molecular weight 2 million, both products of Union Carbide Chemicals and Plastics Company Inc. of Danbury, Conn., USA. For agents of low water solubility, release of the agent from the matrix may be achieved at least in part by erosion of the matrix. Poly(ethylene oxide) matrices can be made more erodible by the inclusion poly(ethylene oxide) of a lower molecular weight (less than 1,000,000). Mixtures of polyethylene oxides of different molecular weights can also be used regardless of the water solubility of the agent.

Polysaccharide gums suitable for use in this invention include both natural and modified (semi-synthetic) polysaccharide gums. Examples are dextran, xanthan gum, gellan gum, welan gum and rhamsan gum. Xanthan gum is preferred.

Crosslinked polyacrylic acids of greatest utility are those whose properties are the same as those described above for alkyl-substituted cellulose and polyalkylene oxide polymers. Preferred crosslinked polyacrylic acids are those with a viscosity ranging from about 4,000 to about 40,000 centipoise for a 1% aqueous solution at 25□ C. Three presently preferred examples are CARBOPOL® NF grades 971P, 974P and 934P (BFGoodrich Co., Specialty Polymers and Chemicals Div., Cleveland, Ohio, USA). Further examples are polymers known as WATER LOCK®, which are starch/-acrylates/-acrylamide copolymers available from Grain Processing Corporation, Muscatine, Iowa, USA.

The hydrophilicity and water swellability of these polymers cause the drug-containing matrices to swell in size in the gastric cavity due to ingress of water in order to achieve a size that will be retained in the stomach when introduced during the fed mode. These qualities also cause the matrices to become slippery, which provides resistance to peristalsis and further promotes their retention in the stomach. For highly soluble drugs, the release rate of a drug from the matrix is primarily dependent upon the rate of water imbibition and the rate at which the drug dissolves and diffuses from the swollen polymer, which in turn is related to the solubility and dissolution rate of the drug, the drug particle size and the drug concentration in the matrix. For sparingly soluble drugs, the release rate of a drug from the matrix is primarily dependent upon the rate of water imbibition and the rate at which the polymer dissolves in the gastrointestinal fluid or erodes due to the action of the fluid. Also, because these polymers dissolve very slowly in gastric fluid, the matrix maintains its physical integrity over at least a substantial period of time, in many cases at least 90% and preferably over 100% of the dosing period. The particles will then slowly dissolve or decompose. Complete dissolution or decomposition may not occur until 24 hours or more after the intended dosing period ceases, although in most cases, complete dissolution or decomposition will occur within 10 to 24 hours after the dosing period. For erodible systems, where the main mechanism of drug release is through dissolution of the polymer, dissolution may occur within 2 to 8 hours.

The drug is preferably dispersed homogeneously in the polymeric matrix, although this is not a requirement of the present invention. The weight ratio of drug to polymer is not critical and may vary. In most cases, however, best result will be obtained with a drug:polymer weight ratio within the range of about 1:9 to about 9:1, preferably about 1:1 to about 9:1, and most preferably about 4:1 to about 9:1. For highly potent drugs, a much lower ratio may be used.

The particles are preferably consolidated into a packed mass for ingestion, even though they will separate into individual particles once ingested. Conventional methods can be used for consolidating the particles in this manner. For example, the particles can be placed in gelatin capsules known in the art as "hard-filled" capsules and "soft-elastic" capsules. The compositions of these capsules and procedures for forming them are known among those skilled in drug formulations. The encapsulating material should be highly soluble in gastric fluid so that the particles are rapidly dispersed in the stomach after the capsule is ingested.

One presently preferred dosage form is a size 0 gelatin capsule containing either two or three pellets of drug-impregnated polymer. For two-pellet capsules, the pellets are cylindrically shaped, 6 mm in diameter and 10.5 mm in length. For three-pellet capsules, the pellets are again cylindrically shaped, 6 mm in diameter and 7 mm in length. For a size 00 gelatin capsule with two pellets, the pellets are cylindrical, 7.5 mm in diameter and 11.75 mm in length. For a size 00 gelatin capsule with three pellets, the pellets are cylindrical, 7.5 mm in diameter and 4.8 mm in length. These are merely examples; the shapes and sizes can be varied considerably.

The drugs that serve as therapeutic agents in the oral drug dosage forms of this invention range from those of low solubility in gastric fluid, to those of intermediate solubility and those of high solubility. The dosage form may be adapted to each case.

With drugs of low or limited solubility, it is preferred that portions of the drug be retained in the matrix in solid form for at least about two hours, and yet the drug must be sufficiently soluble to permit the diffusion required to achieve its therapeutic effect. The solubility should thus be high enough to permit diffusion of the drug from the particle at a rate fast enough to provide an effective level of therapy yet slow enough to extend the treatment over the desired duration. Low solubility drugs of particular interest are those whose solubility (determined in water at 37° C.) lies within the range of about 0.005% to about 10% by weight, and preferably from about 0.1% to about 5% by weight.

Included among these drugs are those that are effective in eradicating *Helicobacter pylori* from the submucosal tissue of the gastrointestinal tract, particularly the stomach. The oral dosage form of this invention improves the effectiveness of these drugs in treating stomach and duodenal ulcers as well as gastritis and esophagitis, and in reducing the risk of gastric carcinoma. Drugs and drug combinations suggested for these indications include bismuth salts such as bismuth subsalicylate or bismuth citrate, metronidazole, and amoxycillin, other antibiotics such as clarithromycin, thiamphenicol, tetracycline, neomycin or erythromycin, H-2 antagonists such as cimetidine or ranitidine, proton pump inhibitors such as omeprazole, and combinations of these drugs. Preferred drugs for this indication are clarithromycin plus omeprazole, a bismuth salt plus metronidazole, amoxycillin plus metronidazole, and amoxycillin or a bismuth salt plus omeprazole.

Sustained-release dosage forms in accordance with this invention are also of particular value in the administration of drugs such as peptides and proteins that are labile upon exposure to gastric pH or gastric enzymes. These drugs and others of a similarly large molecular size are most efficiently absorbed in the region extending from the lower stomach through the duodenum to the upper part of the small intestine. The formulations of this invention physically protect the undissolved portion of the drug within the water-swellable matrix until the drug dissolves and is thereby released. This results in continuous delivery of undegraded drug at or near this region of high absorptivity for an extended period of time. Therapeutic agents that otherwise require administration by injection can thus provide effective results when administered orally. Examples of such agents are calcitonin, calcitriol and ceftriaxone sodium. Further examples of therapeutic agents that are not efficiently absorbed from the lower G.I. tract and that will therefore benefit from this invention are captopril, simvastitin, cyclosporins, acyclovir, cephalosporins, interleukins, nitrofurantoin, and the ergot alkaloids.

The delivery of drugs in a continuous and prolonged rather than pulse-wise manner provides improved therapy due to better compliance with less frequent dosing. Continuous and prolonged delivery also offers both a reduction in side effects associated with the drug and the ability to achieve efficacy with less frequency administration. Examples of therapies in which this is useful are as follows:

(1) A reduction in angioedema and agranulocytoses, which are side effects arising from the administration of angiotensin-converting enzyme inhibitors such as enalapril maleate and captopril;

(2) A reduction of anti-cholinergic (drying) and sedative side effects of antihistamines such as clemastine fumarate;

(3) Prolonged activity for cholesterol lowering drugs such as lovastatin with less frequent administration and reduced side effects such as liver dysfunction, rhabdomyolysis, rash and headache;

(4) Prolongation of the effects of antidepressant agents such as fluoxetine, with a reduction of the side effects of insomnia and stomach upset;

(5) With the use of antiepileptic drugs such as carbamazepine, the benefit of only a single daily administration rather than administration three or four times a day as presently required, and a reduction both of side effects and of response variability;

(6) With potent analgesics such as meperidine, the benefit of steady, prolonged control of pain with reduced drug toxicity;

(7) Less frequent administration, and less irritation upon use of blood platelet aggregation inhibitors such as ticlopidine; and (8) With drugs whose absorption is normally low and highly variable, such as cyclosporine, an increase in the amount absorbed and a decrease in variability between patients.

Similar benefits are obtained with other types of drugs. Calcium channel blockers, such as verapamil, diltiazem, nifedipine, or nicardipine, for example, can be administered with controlled delivery and gastric retention to extend their effects through the night and thereby alleviate early morning hypertension, the cause of many heart attacks. The frequency of administration can also be reduced to a single daily dose. The invention also enhances the treatment of gastroesphageal reflux disease by providing prolonged, localized effects of agents such as pentagastrin, PG-F2, and metaclopramide that improves the competency of lower esophageal sphincter (LES) muscles.

Other drugs that will benefit from the invention include H-2 antagonists such as cimetidine and ranitidine, or calcuim carbonate, for ulcer treatment and prevention; non-steroidal anti-inflammatory agents (NSAIDS) such as indomethacin, ibuprofen, naproxen and piroxicam; steroids such as prednisone, prednisolone and dexamethasone; other NSAIDS such as diclofenac and ketorolac; acyclovir for the treatment of viral diseases such as herpes; tamoxifen for treatment of cancer; chlorpheniramine maleate for allergic disorders; potassium chloride for potassium supplementation, and peptides or other labile molecules such as protease inhibitors for treatment of AIDS. Still further drugs will be apparent to those skilled in pharmacology.

In aspects of this invention that are directed to highly soluble drugs, the drugs thus addressed are those that are characterized by the United States Pharmacopeia XXII as at least "freely soluble" in water, i.e., drugs whose solubility is greater than one part of the drug in about twenty parts of water. Drugs of particular interest are those whose solubility is greater than one part in about ten parts of water, and drugs of even greater interest are those whose solubility is greater than one part in about three parts of water. The parts referred to in this paragraph and throughout this specification are parts by weight. Examples of drugs of high solubility to which this invention is applicable are metformin hydrochloride, vancomycin hydrochloride, captopril, erythromycin lactobionate, ranitidine hydrochloride, sertraline hydrochloride, ticlopidine hydrochloride, amoxicillin, cefuroxime axetil, cefaclor, clindamycin, doxifluridine, tramadol, fluoxitine hydrochloride, ciprofloxacin, gancyclovir, bupropion, lisinopril, and esters of ampicillin. Examples of drugs of low solublity to which this invention is applicable are cefaclor, ciprofloxacin, saguinavir, ritonavir, nelfinavir, clarithromycin, azithromycin, ceftazidine, cyclosporin, digoxin, paclitaxel, iron salts, topiramate, and ketoconazole. Other drugs suitable for use and meeting the solubility criteria described above will be apparent to those skilled in the art. Drugs of particular interest are metformin hydrochloride and sertraline hydrochloride. The drug loadings (weight percent of drug relative to total of drug and polymer) in most of these cases will be about 80% or less.

The invention is also of use with drugs that have been formulated to include additives that impart a small degree of hydrophobic character, to further retard the release rate of the drug into the gastric fluid. One example of such a release rate retardant is glyceryl monostearate. Other examples are fatty acids and salts of fatty acids, one example of which is sodium myristate. The quantities of these additives when present can vary; and in most cases, the weight ratio of additive to drug will range from about 1:20 to about 1:1, and preferably from about 1:8 to about 1:2.

The particulate drug/polymer mixture or drug-impregnated polymer matrix can be prepared by various conventional mixing and comminution techniques readily apparent to those skilled in the chemistry of drug formulations. Examples of such techniques are as follows:

(1) Direct compression, using appropriate punches and dies, such as those available from Elizabeth Carbide Die Company, Inc., McKeesport, Pa., USA; the punches and dies are fitted to a suitable rotary tableting press, such as the Elizabeth-Hata single-sided Hata Auto Press machine, with either 15, 18 or 22 stations, and available from Elizabeth-Hata International, Inc., North Huntington, Pa., USA; and (2) Injection or compression molding using suitable molds fitted to a compression unit, such as those available from Cincinnati Milacron, Plastics Machinery Division, Batavia, Ohio, USA.

When particles are made by direct compression, the addition of lubricants may be helpful and sometimes important to promote powder flow and to prevent capping of the particle (breaking off of a portion of the sphere) when the pressure is relieved. Useful lubricants are magnesium stearate (in a concentration of from 0.25% to 3% by weight, preferably less than 1% by weight, in the powder mix), and hydrogenated vegetable oil (preferably hydrogenated and refined triglycerides of stearic and palmitic acids at about 1% to 5% by weight, most preferably about 2% by weight. Additional excipients may be added to enhance powder flowability and reduce adherence.

Different drugs have different biological half-lives, and the frequency of administration needed for effective use of any single drug depends on the half-life of that drug. When two or more drugs are co-administered in a single dose using dosage forms of the prior art, an unfavorable compromise is often required, resulting in an underdose of one drug or an overdose of the other. The multi-particle dosage form of this invention permits different drugs to be placed in different matrix particles, each particle individually formulated to provide the release rate and duration that are optimal for the particular drug carried by that particle. This can be done by varying the matrix composition, the particle size, the particle molecular weights, or any other characteristic that affects the release rate and duration. The number of particles carrying individual drugs can also be varied among the different drugs. For example, a capsule made from three particles may contain two particles carrying one drug and one particle carrying the other drug.

Examples of drug combinations for which the formulations of this invention are useful are norethindrone plus ethinyl estradiol, a combination useful for fertility control, acetaminophen plus codeine (a potent analgesic combination), captopril plus hydrochlorthiazide (a useful cardiovascular combination), clarithromycin plus omeprazole (for the eradication of H. pylori), and prednisolone plus cylosporine (used for organ transplantation). In these and other examples, each ingredient can be individually formulated to achieve a release rate that is optimal for the pharmacokinetics and biological activity of each drug. This invention is also useful as a means of co-administering drugs that cannot otherwise be combined in a single dosage form due to their chemical incompatibility.

The following examples are offered for purposes of illustration, and are not intended to limit or to define the invention in any manner. All percents are by weight unless otherwise indicated.

EXAMPLE 1

Four dogs, all male beagles ranging in age from 10 months to 21 months and weighing from 6 kg to 10 kg each, were housed individually and each was fed a 1:1 (weight ratio) wet:dry mixture of food weighing 300 g once daily at 3:00 p.m. Water was provided ad libitum. The dogs were fasted for 6-8 hours overnight, preceded by the removal of feces and any uneaten food.

Test formulations were administered in various regimens. In some of the tests, the dogs were given an immediate release (IR) regimen in the form of a single gelatin capsule containing a test species in a selected amount. A simulated controlled release (SCR) regimen was used in other tests by administering a gelatin capsule containing a test species in a selected amount every half hour. A third regimen was a controlled release (CR) regimen, in which the test species was incorporated in a compressed tablet of POLYOX 303 and magnesium stearate. (The arginine controlled-release dosage form, for example, contained 300 mg arginine, 62.5% POLYOX 303 and 0.5% magnesium stearate, for a total weight of 800 mg, compressed after dry blending into a tablet measuring 7.94× 19.05 mm. A test in which the table was immersed in simulated gastric fluid indicated that 55% of the arginine was released from this table within six hours.) Fifteen minutes after the administration of the test formulations in all cases (or after the beginning of the administration regimen), each dog ingested two swelling tablets (weighing 400 mg and 800 mg, respectively, and measuring 6.15×16.26 mm and 7.94×19.05 mm, respectively), each such tablet containing 25% barium sulfate (a radiopaque compound). The barium tablets were visualized every thirty minutes by fluoroscopy until they left the stomach. The time of the last observation of the 800 mg tablet in the stomach was recorded as the retention time. The test group also included a negative control using a fasted dog with no test formulations administered, and a positive control using a dog that was fed a standard 50 g meal but no test formulations.

The test results in terms of the retention times in hours are shown in Table I, which lists the means of the results observed among the four dogs as well as the range among the dogs for each test.

TABLE I

Fed Mode Inducing Agents and Resulting Retention Times for 7.94 × 19.05 mm BaSO$_4$ Tablet

| | | | Retention Time (h) | |
|---|---|---|---|---|
| Test Agent | Dosage (mg) | Regimen[a] | Mean | Range |
| None-fasted (Negative Control) | — | — | 0.9 ± 0.6 | 0.5-1.7 |
| None-fed (Positive Control) | — | — | 4.1 ± 0.8 | 3-4.5 |
| Glycine hemihydrochloride | 800 | IR | 3.1 ± 2.0 | 1.5-6 |
| Xylitol | 600 | IR | 3.1 ± 1.5 | 1.5-5 |
| Na docusate | 200 | IR | 2.6 ± 1.4 | 1-4.5 |

TABLE I-continued

Fed Mode Inducing Agents
and Resulting Retention Times for 7.94 × 19.05 mm BaSO$_4$ Tablet

| | | | Retention Time (h) | |
|---|---|---|---|---|
| Test Agent | Dosage (mg) | Regimen[a] | Mean | Range |
| β-Casomorphin | 25 | IR | 2.6 ± 1.1 | 1.5-4 |
| α-Lipoic acid | 150 | IR | 2.8 ± 1.6 | 1.5-5 |
| Loperamide | 0.1 | IR | 2.5 ± 1.3 | 1.5-4 |
| L-Arginine | 300 | CR[b] | 3.6 ± 1.6 | 2.5-6 |
| L-Arginine | 400 | IR | 1.6 ± 0.2 | 1.5-2 |
| Trp-Trp | 20 | SCR[c] | 2.8 ± 0.3 | 2.5-3 |
| Trp-Trp | 200 | IR | 3.1 ± 3.9 | 0.5-9 |
| Trp-Trp | 200 | IR | 2.1 ± 1.8 | 1-4.75 |

[a]IR: immediate release; CR: controlled release; SCR: simulated controlled release.
[b]The amount of arginine released by this formulation over a six-hour period was estimated at approximately 150 mg.
[c]Simulated controlled release was achieved by administering 20 mg of the agent every thirty minutes.

EXAMPLE 2

Further tests were performed on a second group of dogs, consisting of five female beagles one year in age and weighing 5-7 kg each. The test protocols were the same as those in Example 1 except that the dogs were fasted for 24 hours before each test, and the test results are listed in Table II below, which lists the mean of the results observed among the five dogs as well as the range among the dogs for each test.

TABLE II

Fed Mode Inducing Agents
and Resulting Retention Times for 7.94 × 19.05 mm BaSO$_4$ Tablet

| | | | Retention Time (h) | |
|---|---|---|---|---|
| Test Agent | Dosage (mg) | Regimen | Mean | Range |
| None-fasted (Negative Control) | — | — | 1.0 ± 0.2 | 0.75-1.25 |
| None-fed (Positive Control) | — | — | 5.4 ± 0.9 | 4-6 |
| Trp-Trp | 5 | SCR[a] | 4.6 ± 1.5 | 2.25-5.75 |
| Trp-Trp | 10 | SCR[b] | 2.4 ± 1.8 | 0.25-4.75 |
| Trp-Trp | 40 | SCR[c] | 3.4 ± 1.9 | 1.25-5.25 |
| Cetylpyridinium chloride | 20 | IR | 4.5 ± 2.6 | 0.75-6.75 |
| Cetylpyridinium chloride | 50 | IR | 4.0 ± 1.3 | 1.75-4.75 |
| Cetylpyridinium chloride | 100 | IR | 3.2 ± 0.9 | 2.75-4.25 |
| Gentian root (gentisic acid) | 200 | IR | 2.6 ± 1.4 | 1.25-4.75 |

[a]Simulated controlled release was achieved by administering 5 mg of the agent every thirty minutes.
[b]Simulated controlled release was achieved by administering 10 mg of the agent every thirty minutes.
[c]Simulated controlled release was achieved by administering 40 mg of the agent every thirty minutes.

EXAMPLE 3

Further tests were performed on the second group of dogs, consisting of five female beagles one year in age and weighing 5-7 kg each. The test protocols were the same as those in Example 2, except that the controls were replaced by a negative control consisting of AVICEL (microcrystalline cellulose, FMC Corporation, Philadelphia, Pa., USA), administered as a simulated controlled release at 10 mg every half hour. The test results are listed in Table III below, which lists the mean of the results observed among the five dogs as well as the range among the dogs for each test.

TABLE III

Fed Mode Inducing Agents
and Resulting Retention Times for 7.94 × 19.05 mm BaSO$_4$ Tablet

| | | | Retention Time (h) | |
|---|---|---|---|---|
| Test Agent | Dosage (mg) | Regimen | Mean | Range |
| AVICEL (Negative Control) | 10 | SCR[a] | 1.4 ± 0.6 | 0.75-1.75 |
| Cetylpyridinium chloride | 20 | IR | 4.45 ± 2.6 | 0.75-6.75 |
| Cetylpyridinium chloride | 5 | IR | 4.0 ± 2.8 | 0.25-6.25 |
| Glycine hemihydrochloride | 20 | SCR[b] | 3.3 ± 1.3 | 1.75-5.25 |
| Glycine hemihydrochloride | 50 | SCR[c] | 3.8 ± 2.6 | 0.75-5.75 |
| Glycine hemihydrochloride | 5 | SCR[d] | 4.0 ± 1.8 | 1.25-6.25 |
| Trp-Trp | 2 | SCR[e] | 4.2 ± 1.1 | 2.75-5.25 |
| Trp-Trp | 0.5 | SCR[f] | 4.6 ± 1.7 | 2.25-6.25 |
| Aspartame | 200 | IR | 3.8 ± 2.3 | 1.75-5.25 |
| β-Casomorphin | 10 | IR | 3.5 ± 2.1 | 1.25-5.75 |

[a]Simulated controlled release was achieved by administering 10 mg of the agent every thirty minutes.
[b]Simulated controlled release was achieved by administering 20 mg of the agent every thirty minutes.
[c]Simulated controlled release was achieved by administering 50 mg of the agent every thirty minutes.
[d]Simulated controlled release was achieved by administering 5 mg of the agent every thirty minutes.
[e]Simulated controlled release was achieved by administering 2 mg of the agent every thirty minutes.
[f]Simulated controlled release was achieved by administering 0.5 mg of the agent every thirty minutes.

The foregoing is offered primarily for purposes of illustration. It will be readily apparent to those skilled in the art that the components, proportions, dosages, formulations, and other parameters of the compositions and methods disclosed herein can be modified further or substituted in various ways without departing from the spirit and scope of the invention.

What is claimed is:

1. A method for pharmacologically inducing the fed mode in a subject, said subject being a human or a dog weighing at least 5 kg, said method comprising administering to said subject a fed mode inducing agent selected from the group consisting of
   alkali and alkaline earth metal docusates,
   said administration being in an amount and a manner that causes release of the fed mode inducing agent in the stomach and retention of the fed mode inducing agent in the stomach so as to cause onset of the fed mode in said subject.

2. A method in accordance with claim 1 in which said fed mode inducing agent is a member selected from the group consisting of calcium docusate and sodium docusate.

3. A method in accordance with claim 1 in which said fed mode inducing agent is sodium docusate.

4. A method in accordance with claim 1 in which the amount of said fed mode inducing agent is from about 30 mg to about 1000 mg.

5. A method in accordance with claim 1 in which the amount of said fed mode inducing agent is from about 60 mg to about 400 mg.

* * * * *